United States Patent
Laguzzi

(10) Patent No.: US 9,782,502 B2
(45) Date of Patent: Oct. 10, 2017

(54) INPUT OR OUTPUT OF AN ELECTRON BEAM STERILISATION DEVICE AND STERILISATION METHOD

(75) Inventor: Fulvio Laguzzi, Alessandria (IT)

(73) Assignee: GUALA PACK S.P.A., Castellazzo Bormida (IT)

( * ) Notice: Subject to any disclaimer, the term of this patent is extended or adjusted under 35 U.S.C. 154(b) by 921 days.

(21) Appl. No.: 14/112,250

(22) PCT Filed: Apr. 17, 2012

(86) PCT No.: PCT/IB2012/051904
§ 371 (c)(1),
(2), (4) Date: Oct. 17, 2013

(87) PCT Pub. No.: WO2012/147008
PCT Pub. Date: Nov. 1, 2012

(65) Prior Publication Data
US 2014/0037498 A1     Feb. 6, 2014

(30) Foreign Application Priority Data
Apr. 26, 2011 (IT) .................. BS2011A0061

(51) Int. Cl.
*A61L 2/08*  (2006.01)
*B65B 55/00*  (2006.01)
*B65B 55/16*  (2006.01)
*A61L 2/24*  (2006.01)
*G21K 5/10*  (2006.01)

(52) U.S. Cl.
CPC .................. *A61L 2/087* (2013.01); *A61L 2/24* (2013.01); *G21K 5/10* (2013.01); *A61L 2202/121* (2013.01); *A61L 2202/122* (2013.01); *A61L 2202/23* (2013.01)

(58) Field of Classification Search
CPC .................. A61L 2/087; B65B 55/16
USPC .......................................... 422/22
See application file for complete search history.

(56) References Cited

U.S. PATENT DOCUMENTS

| 2,040,726 | A | * | 5/1936 | Ball ................ B65B 31/025 426/397 |
| 5,434,421 | A | | 7/1995 | Burth et al. |
| 6,139,796 | A | | 10/2000 | Kristiansson et al. |

(Continued)

FOREIGN PATENT DOCUMENTS

| AU | 740836 B2 | 11/2001 |
| JP | 2002308229 | 10/2002 |

(Continued)

OTHER PUBLICATIONS

English translation of the Abstract for JP 2004/236806 published on Aug. 26, 2004.

(Continued)

*Primary Examiner* — Kevin Joyner
*Assistant Examiner* — Holly Mull
(74) *Attorney, Agent, or Firm* — Thomas Horstemeyer, LLP

(57) ABSTRACT

An electron beam sterilization device (1) for thin-walled containers (C) is fitted with an input (40) or output unit (60) provided with a swivelling body to bring a set of containers (C) from the outside environment into the sterilization chamber or vice versa, avoiding radioactive emissions from the sterilization chamber.

16 Claims, 13 Drawing Sheets

(56) References Cited

U.S. PATENT DOCUMENTS

| | | | |
|---|---|---|---|
| 6,140,657 | A | 10/2000 | Wakalopulos et al. |
| 6,188,075 | B1 | 2/2001 | Takayama et al. |
| 6,833,551 | B2 * | 12/2004 | Avnery .................... G21K 5/10 |
| | | | 250/492.1 |
| 6,885,011 | B2 | 4/2005 | Koenck et al. |
| 7,739,859 | B2 | 6/2010 | Colato et al. |
| 2004/0036039 | A1 | 2/2004 | Miller |
| 2005/0158218 | A1 | 7/2005 | Dumargue et al. |
| 2005/0198924 | A1 | 9/2005 | Benedetti et al. |
| 2006/0151714 | A1 | 7/2006 | Thilly et al. |
| 2006/0159583 | A1 * | 7/2006 | Naslund ................ B65B 55/027 |
| | | | 422/22 |
| 2007/0145304 | A1 | 6/2007 | Roche et al. |
| 2009/0110613 | A1 * | 4/2009 | Naka ....................... A61L 2/087 |
| | | | 422/186 |
| 2009/0134338 | A1 * | 5/2009 | Eguchi ...................... A23L 3/26 |
| | | | 250/396 R |
| 2011/0016829 | A1 | 1/2011 | Drenguis et al. |
| 2011/0101248 | A1 * | 5/2011 | Nishino ................. A61L 2/087 |
| | | | 250/492.3 |

FOREIGN PATENT DOCUMENTS

| | | |
|---|---|---|
| JP | 2004236806 A | 8/2004 |
| JP | 2004532403 A | 10/2004 |
| JP | 2007536174 A | 12/2007 |

OTHER PUBLICATIONS

English translation of the Abstract for JP 2004/532403 published on Oct. 21, 2004.

English translation of the Abstract for JP 2007/536174 published on Dec. 13, 2007.

The International Search Report dated Jul. 4, 2012.

The International Preliminary Report on Patentability dated Aug. 5, 2013.

The International Preliminary Report on Patentability dated Jul. 2, 2013.

Translation of detailed description of Japanese Patent Application JP2003237742A.

* cited by examiner

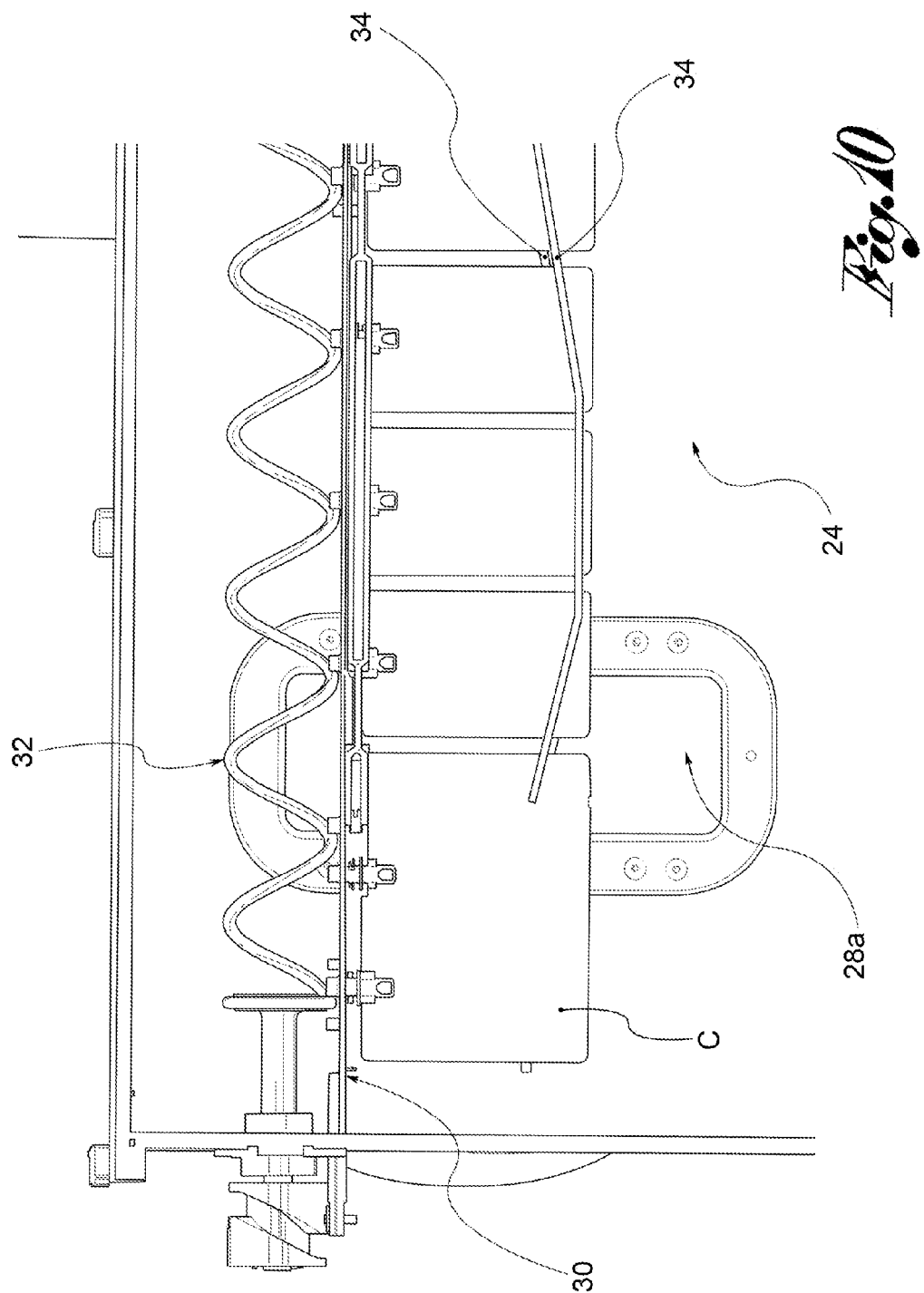

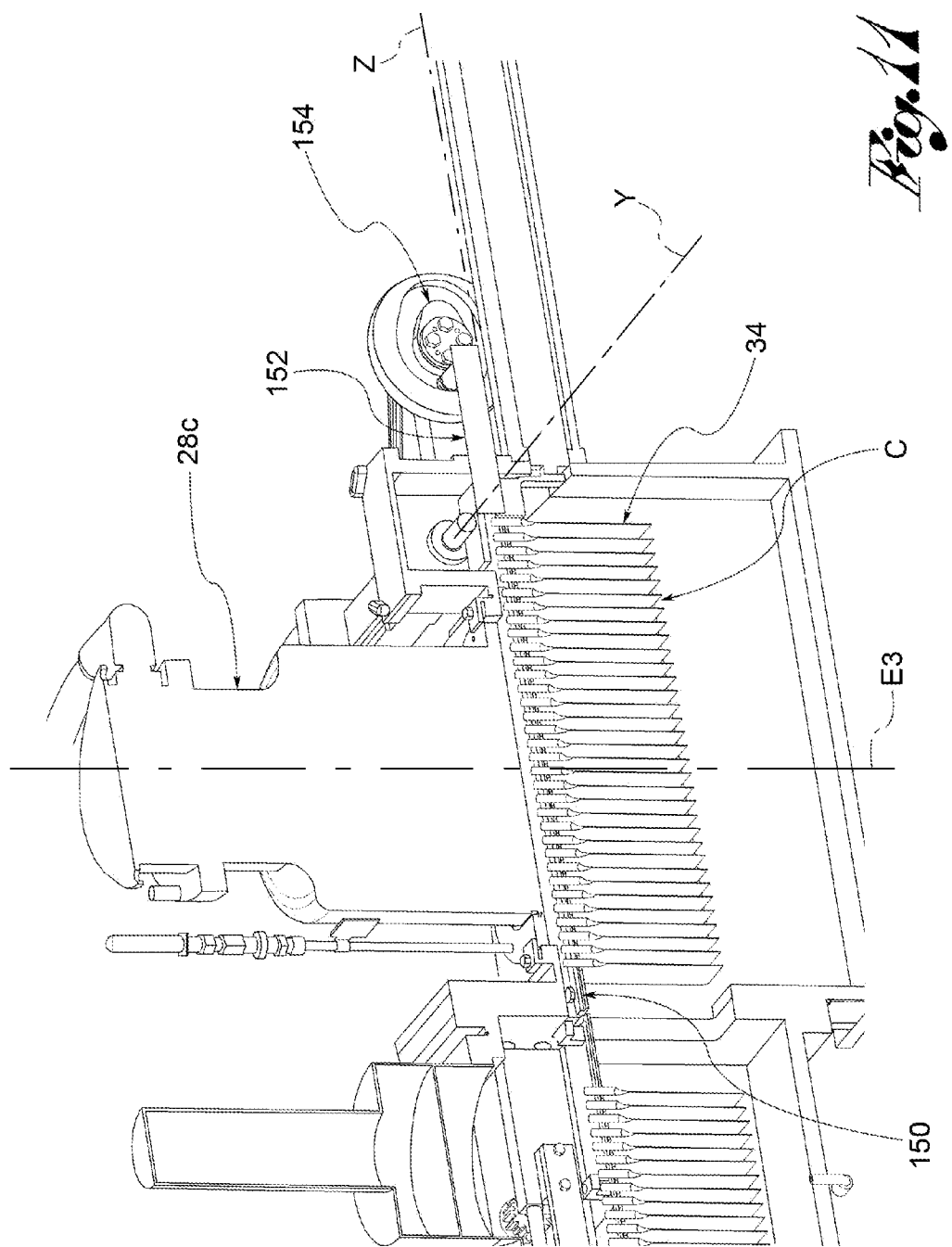

INPUT OR OUTPUT OF AN ELECTRON BEAM STERILISATION DEVICE AND STERILISATION METHOD

CROSS-REFERENCE TO RELATED APPLICATION

This application is the 35 U.S.C. §371 national stage of PCT application PCT/IB2012/051904, filed Apr. 17, 2012 which claims priority to Italian Patent Application No. BS2011A000061, dated Apr. 26, 2011, both of which are incorporated by reference in their entirety.

The present invention relates to a device for sterilising thin wall containers, in particular flexible containers, such as those for containing dense fluids especially foods, such as creams, yoghurt, honey, fruit juices, medicines and the like.

In the food industry, the sterilisation of containers is extremely important for preventing infections and preserving the food contained therein correctly.

Sometimes, chemical sterilisation is performed, during which the container is washed with disinfectants, such as hydrogen peroxide, and then dried, before being sent for subsequent filling operations.

However, chemical sterilisation has some drawbacks such as for instance the presence of residues of the chemical disinfectant in the dry container or the presence of areas which have not been disinfected on account of complicated or irregular geometries of the container. Such drawback is particularly felt in the field of thin-walled flexible containers.

Electron beam sterilisation is becoming increasingly widespread.

Initially, the performance of electron beam sterilisation was restricted to specialised centres, which the containers to be treated had to be sent to and from which the sterilised containers were picked up, with a considerable increase in transport costs and logistics. In such centres high powered (500 kV-10 mV) electron cannons were usually utilised, with all the relative consequences on operator safety and environmental pollution.

Recently, electron beam sterilisation is becoming increasingly popular, thanks to the creation of particularly compact electron cannons functioning efficiently even at low voltages (80-150 kV). Such cannons permit the performance of electron beam sterilisation directly in the container production plant, with notable economic savings.

The purpose of the present invention is to make a low voltage electron beam sterilisation device particularly suitable for treating thin-walled, flexible containers.

The characteristics and advantages of the sterilisation device according to the present invention will be evident from the following description, made by way of a non-limiting example, with reference to the attached drawings, wherein:

FIG. 10 shows a main chamber of the sterilisation group in FIG. 5, at the point of the input unit;

FIG. 11 shows a secondary chamber of the sterilisation group in FIG. 5;

Figure 1:
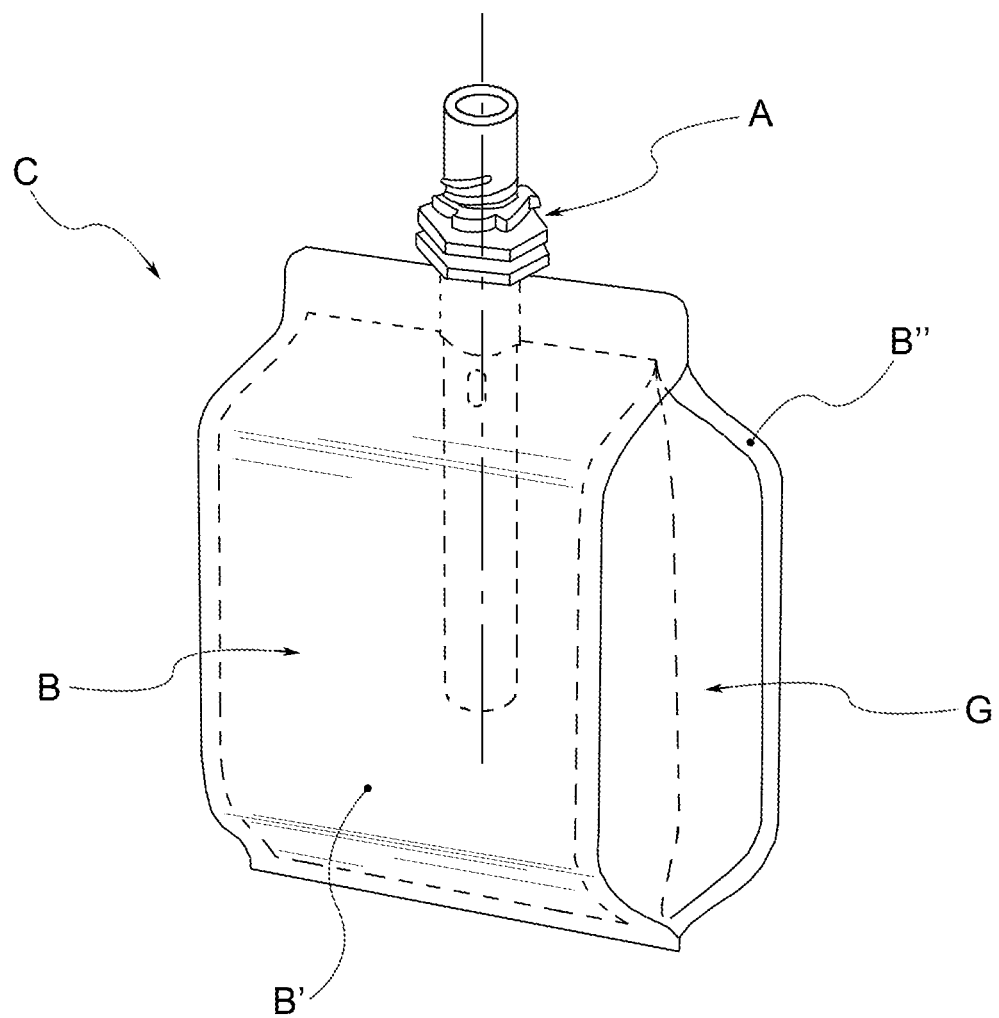
FIGS. 1 and 2 show a specimen of a flexible, thin-walled container, respectively full and empty.

According to the drawings, reference numeral 1 globally denotes a low voltage electron beam sterilisation device for thin-walled, flexible containers.

In particular, the device 1 is suitable for sterilising containers C consisting of a body B formed of two B', B" or more walls of flexible film, facing one another and joined, for example welded along the edges, if required with gusset side walls G, and provided with a straw A in rigid material, fitted in a section of the edge of the body B, usually between the side walls. The straw A projects from the body along a straw axis and may be coupled to a cap, also in rigid material.

Figure 2:
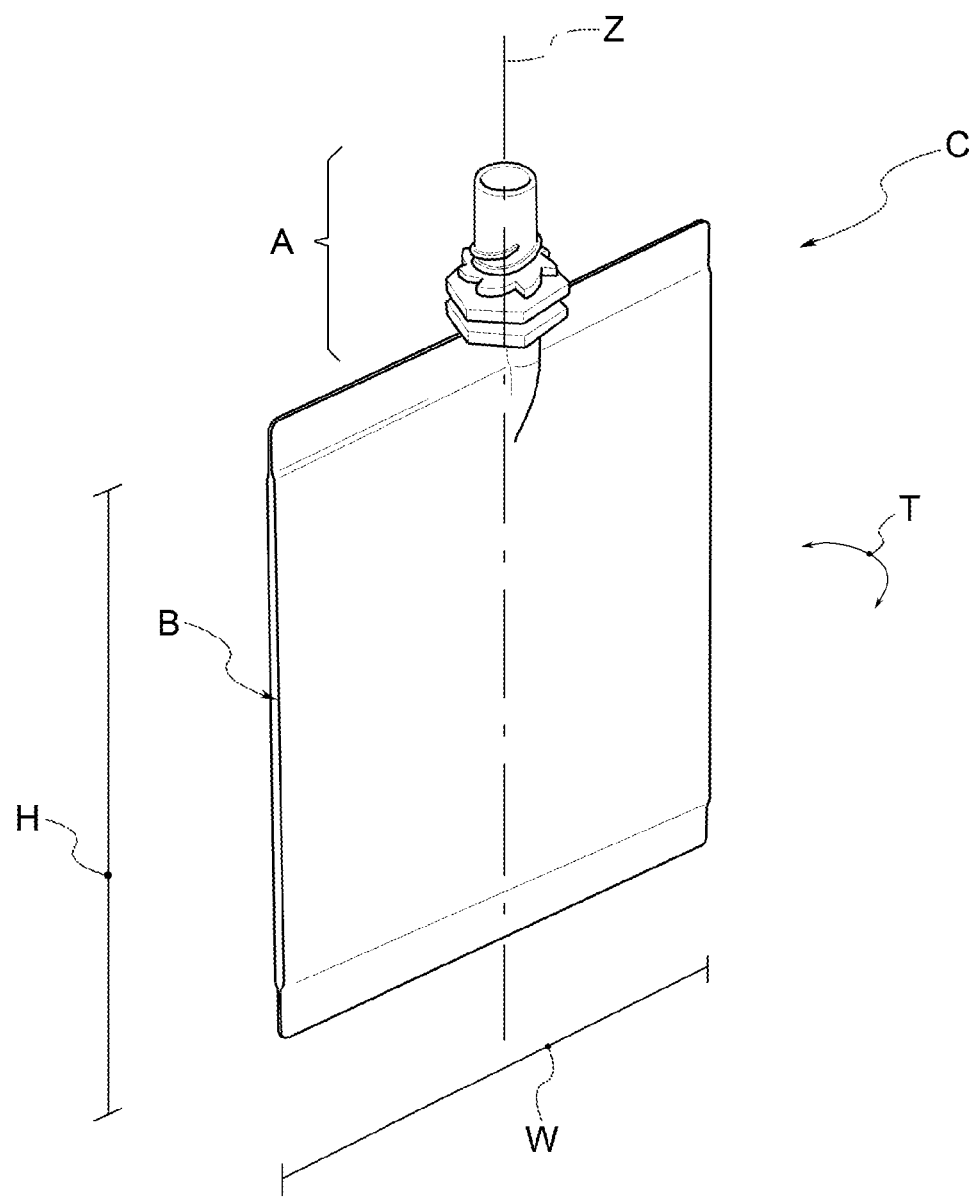
Figure 3:
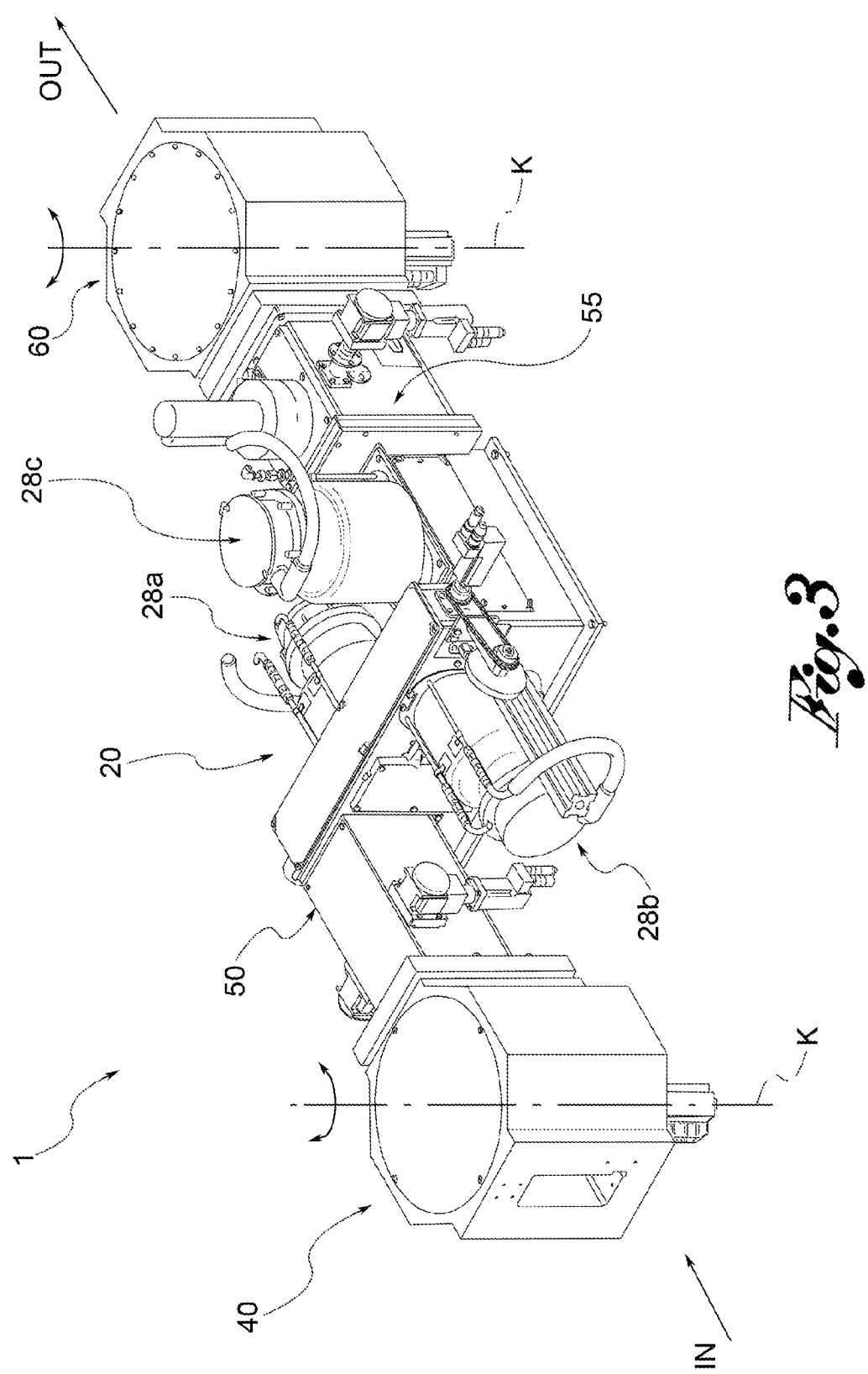
FIG. 3 shows an overall view of the sterilisation device according to the present invention, according to one embodiment.
Figure 4:
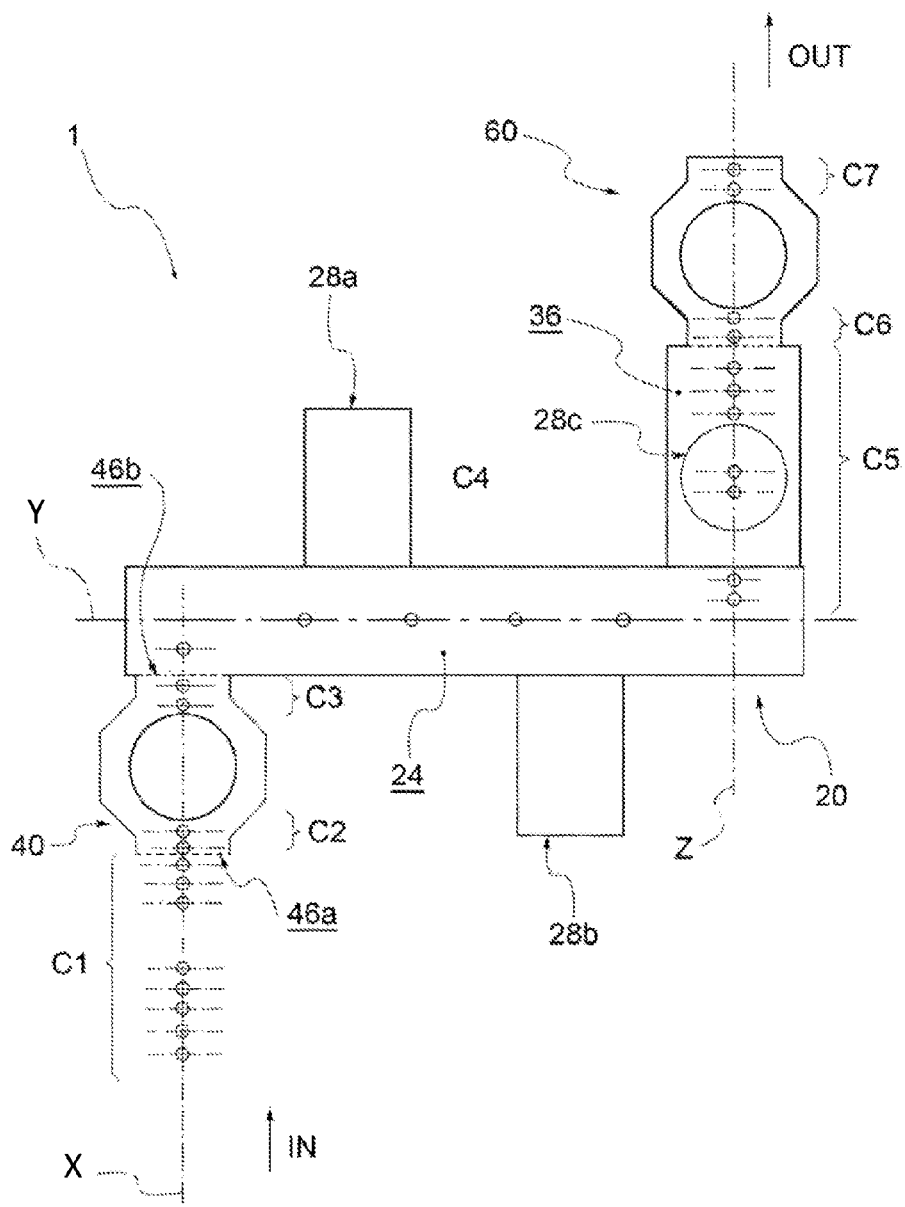
FIG. 4 is a scheme diagram of a layout of the sterilisation device in FIG. 3.
Figure 5:
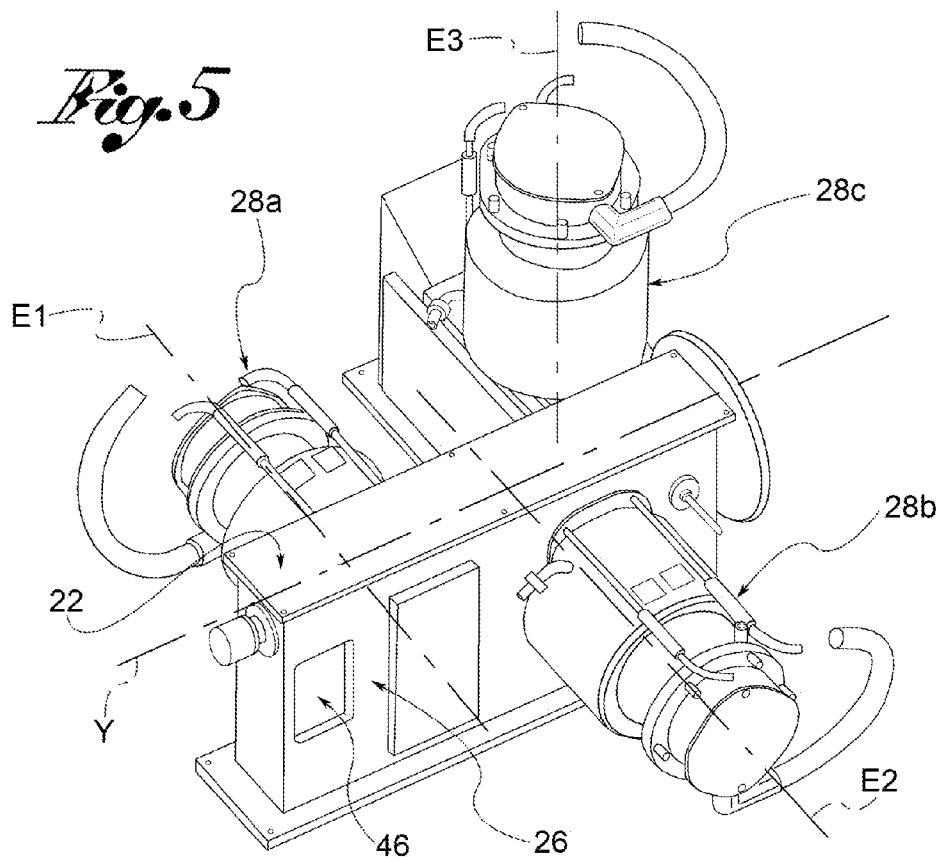
FIG. 5 shows a sterilisation group of the sterilisation device in FIG. 3.
Figure 5A:
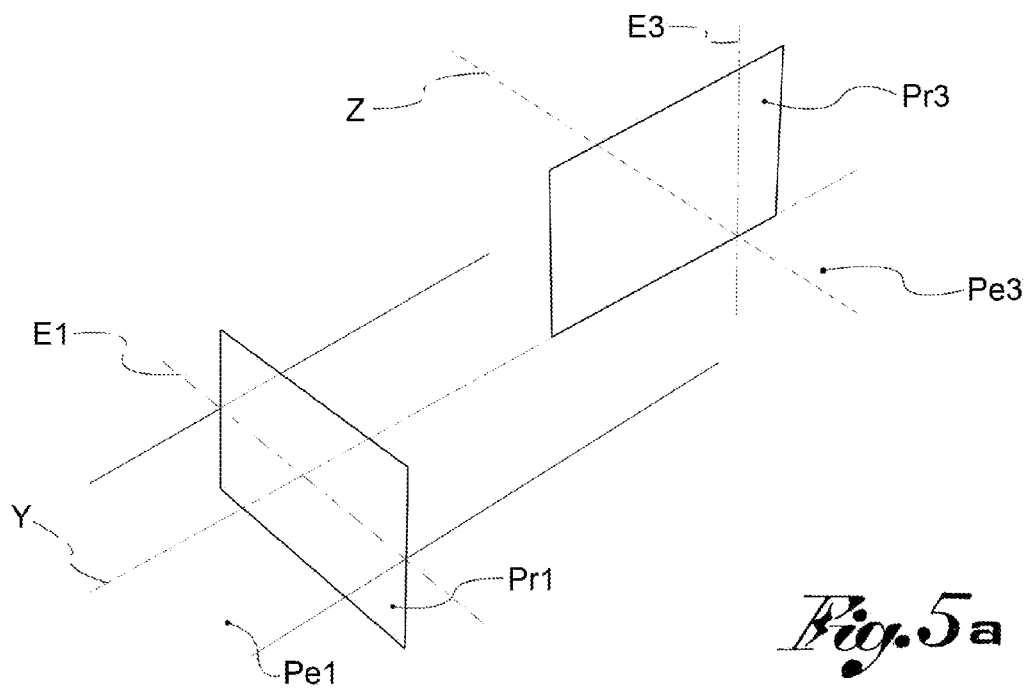
FIG. 5a shows a diagram of the reference planes and the emission planes defined for the present invention.
Figure 6:
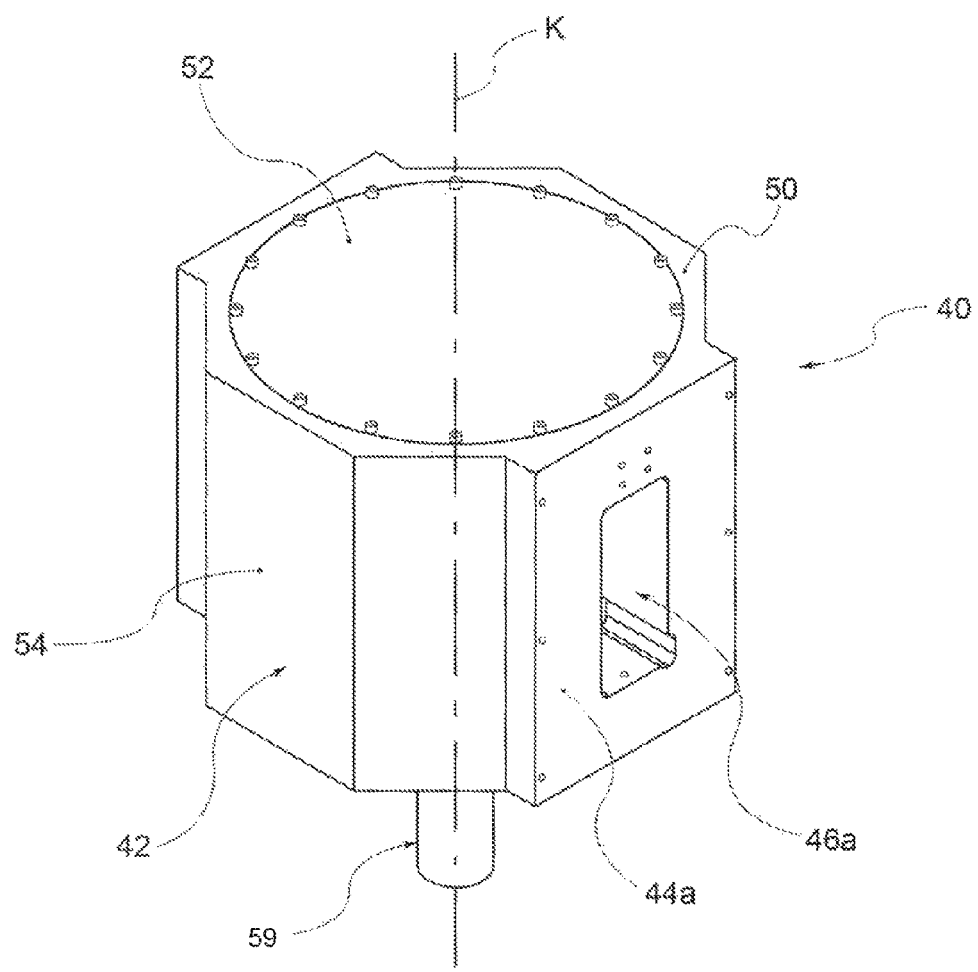
FIG. 6 shows an input unit of the sterilisation device in FIG. 3.
Figure 7:
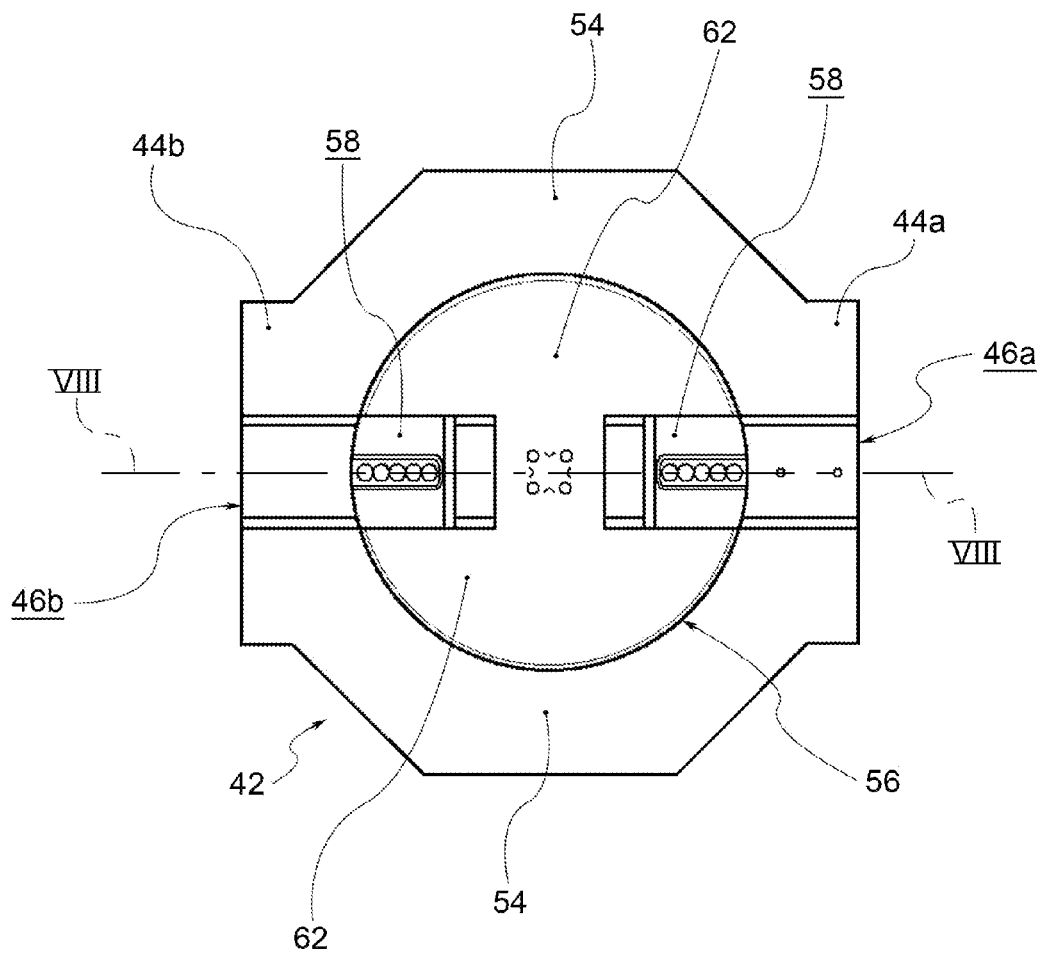
FIG. 7 shows a horizontal cross-section view of the input unit in FIG. 6.
Figure 8:
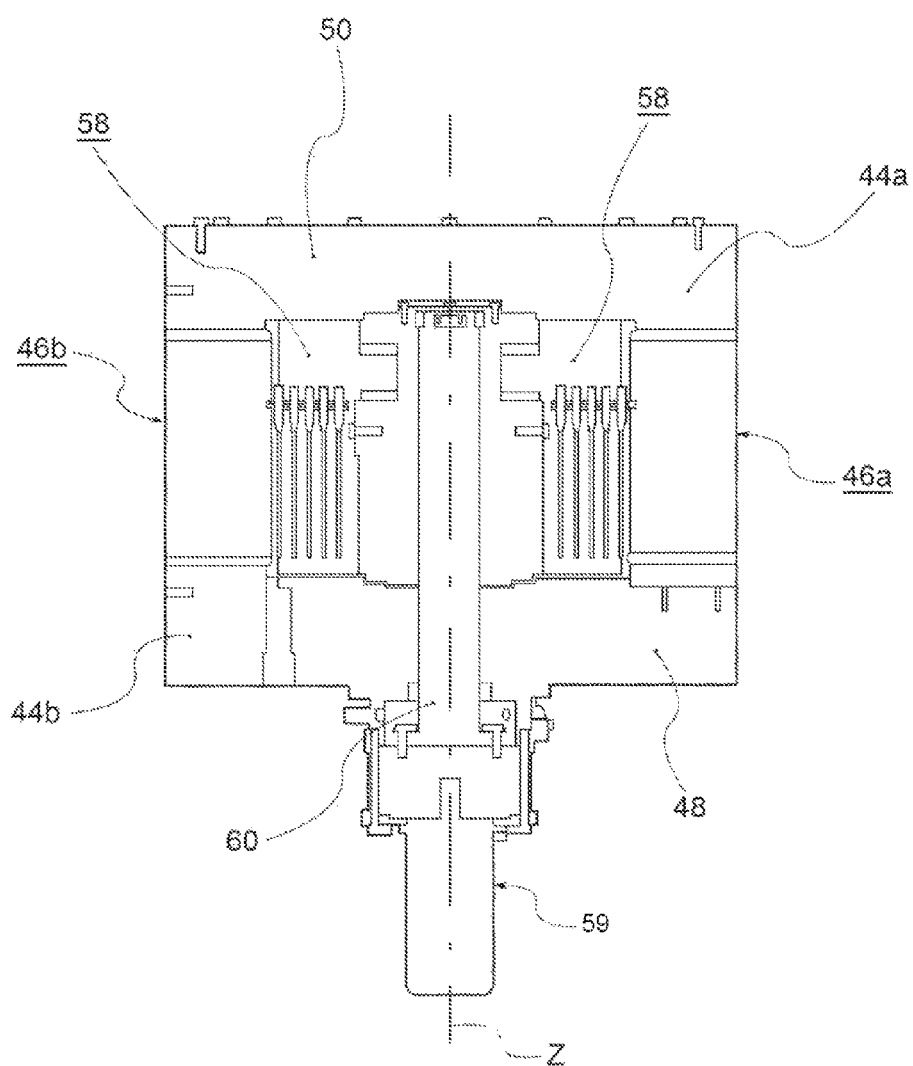
FIG. 8 shows a longitudinal cross-section view of the input unit in FIG. 6, along the section plane VIII-VIII in FIG. 7.
Figure 9:
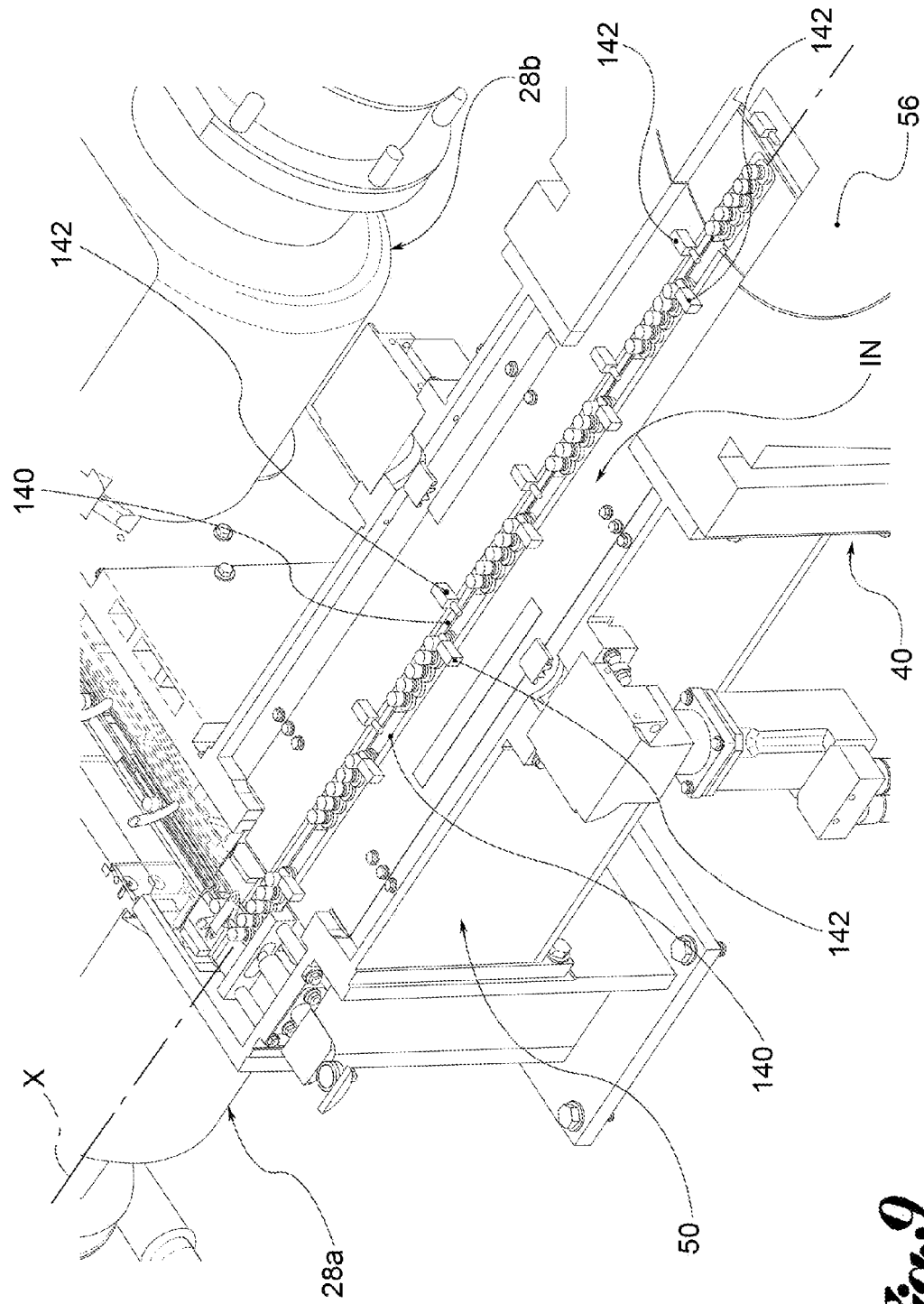
FIG. 9 shows a pre-sterilisation chamber of the device in FIG. 3.
Figure 12A:
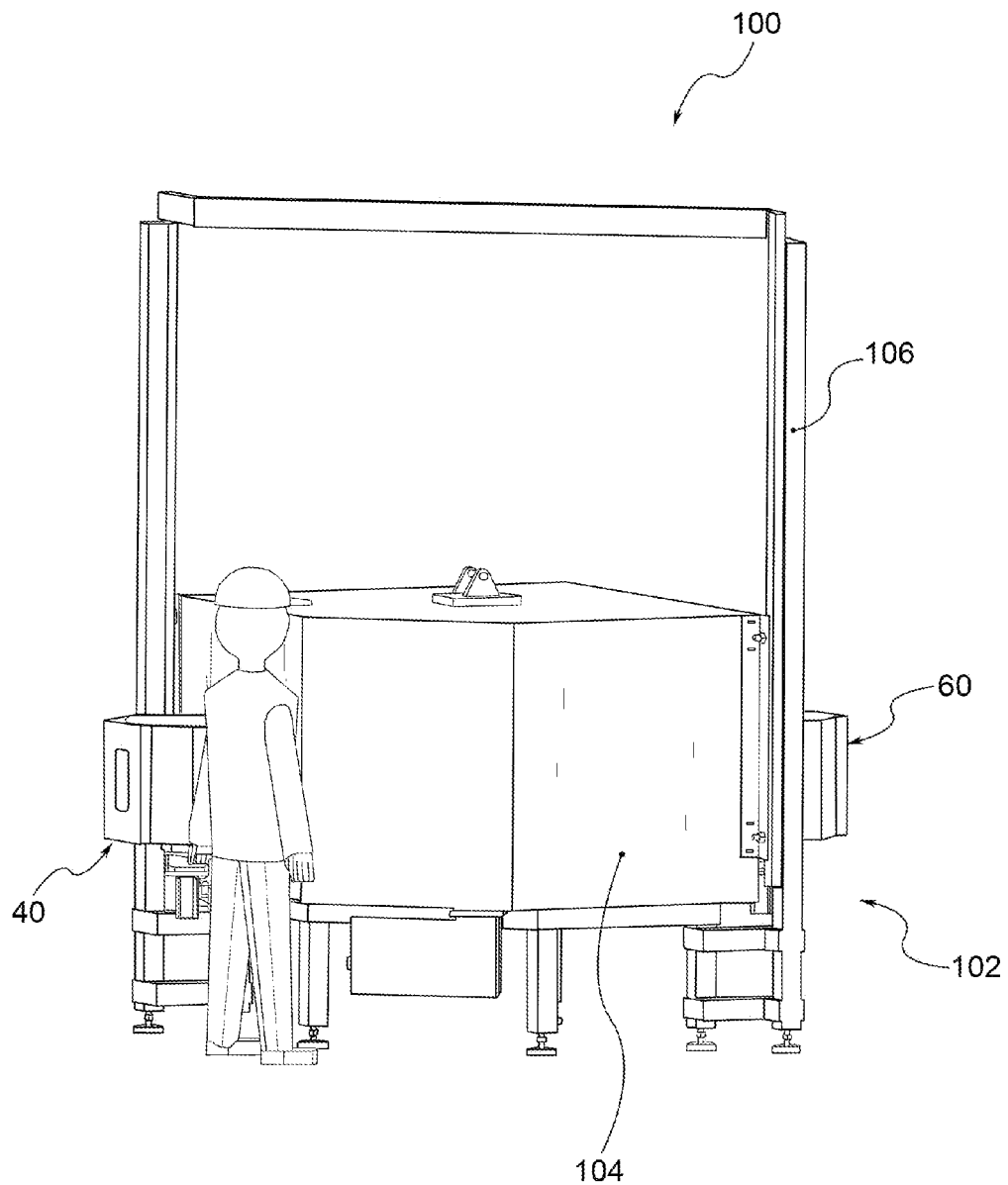
FIGS. 12a and 12b show an example of embodiment of the sterilisation system, fitted with an external, anti-radiation casing, in a closed and open configuration respectively.
Figure 12B:
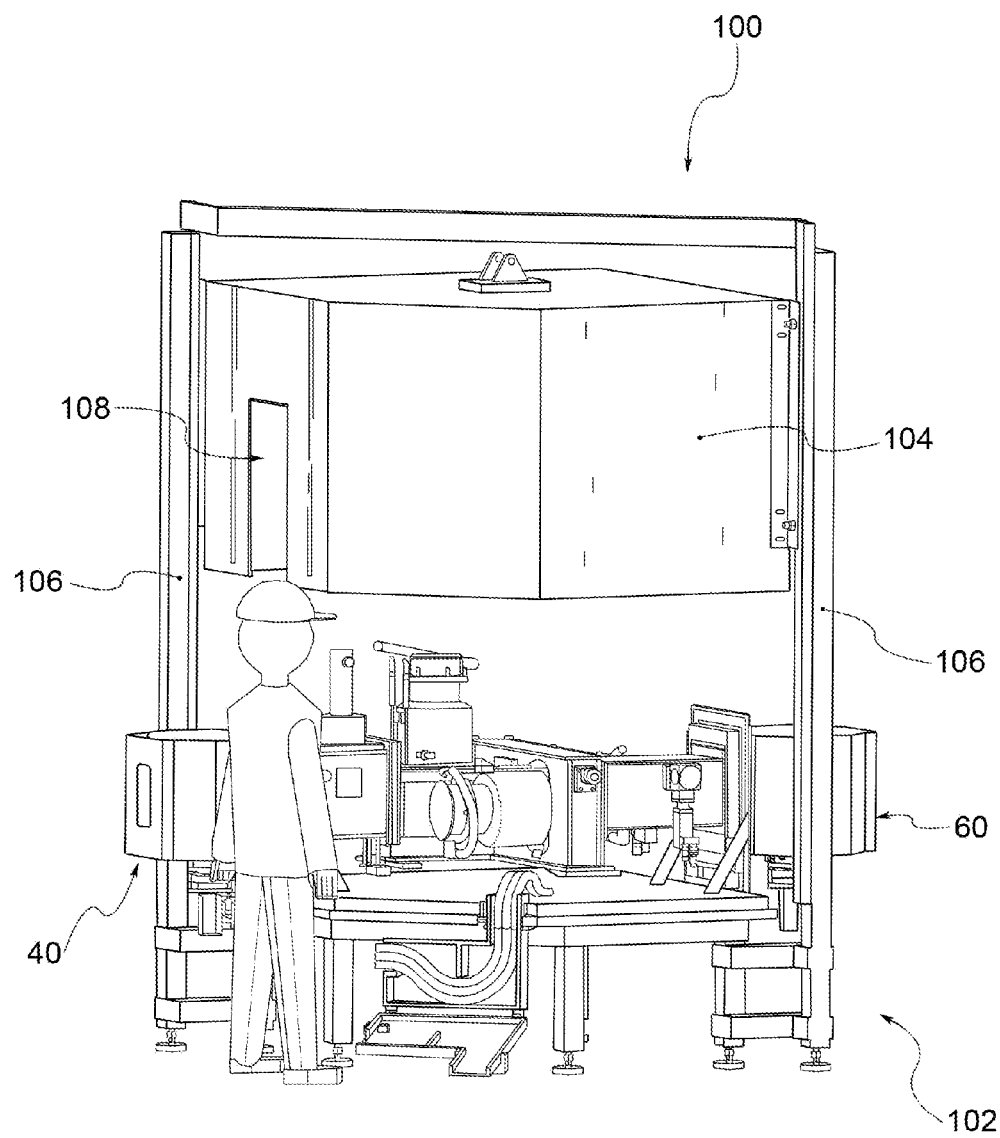

When the flexible container is just made and empty, the body is particularly thin (FIG. 2), while it appears to bulge when filled (FIG. 1).

For the empty containers C, a height H is defined along the straw axis, a width W transversal to the height H, and a thickness T of the thin wall.

One embodiment example of such containers is shown in documents EP-A1-1538105 and U.S. Pat. No. D-552,483, in the Applicant's name; one embodiment example of a straw with cap is shown in the document WO-A1-2008-050361, also in the Applicant's name.

The sterilisation device 1 comprises a sterilisation group 20, in which the sterilisation by means of low voltage electron beams takes place, an input unit 40 for the introducing the containers to be treated in the sterilisation group 20. and an output unit 60 for the exit of the treated containers from the sterilisation group 20.

Said input unit 40 and said output unit 60 also form an obstacle to the leakage of radioactive emissions, and in particular of the X-rays produced by the electron beam inside the sterilisation group 20, at its input and output.

The input unit 40 comprises an outer casing 42 provided with a front wall 44a which an entrance 46a is made in for the entrance of the containers C to be treated, coming from machines upstream of the sterilisation device 1.

Similarly, the outer casing 42 is provided with a back wall 44b which an exit 46b is made in for the entrance of the containers C to be treated in the sterilisation group 20.

The outer casing 42 further comprises a bottom 48 and a cover, preferably fitted with a removable lid 52 for access to the inside of the casing.

The outer casing 42 further comprises side walls 54, preferably polygonal-shaped.

The input unit 40 further comprises a swivelling body 56, housed at least partially in the compartment inside the casing 42, swivelling on command in alternate directions or always in the same direction, around a rotation axis K.

To such purpose, the input unit 40 is fitted with drive means, such as an electric motor 59, preferably of the brushless type connected to the swivelling body 56, preferably positioned under the bottom 48 of the casing 42. For example, the motor 59 is connected to the swivelling body 56 by means of a shaft 60 which crosses the bottom 48 of the outer casing.

The swivelling body 56 has at least one loading seat suitable for receiving at least one container to be treated. In particular, the loading seat can be aligned with the entrance 46 of the casing 42 to enable the loading of containers to be treated.

Preferably the swivelling body 56 has two loading seats 58, for example diametrically opposite each other, which can be alternately aligned with the entrance 46a.

In addition, by rotation on command, the loading seat 58 can be aligned with the exit 46b of the casing for dropping the containers to be treated into the sterilisation group 20.

Preferably when one loading seat is aligned with the exit 46b, another loading seat is aligned with the entrance 46a, so that the loading of containers to be treated from the entrance 46a can take place simultaneously with the emptying of other containers from the exit 46b.

The swivelling body 56 further presents filling portions, outside the loading seats, which occupy the operating area of the swivelling body rotating in the casing, so as to prevent or limit as far as possible the presence of leaks from inside the sterilisation group 20 outwards through the input unit 40.

For example, the swivelling body 56 is a solid cylindrical body in which loadings seats 58 are made, generally diametrically opposite each other, having a radial extension from the periphery towards the inside of the cylindrical body, so as to determine solid portions 62 of operating space in the form of cylindrical segments, which brush the surface of the inner compartment of the casing 42.

The containers to be treated pass into the sterilisation group 20 from the input unit 40.

To such purpose, the sterilisation device 1 comprises extraction means, suitable for extracting the containers housed in the loading seat 58 facing the exit 46b of the input unit 40.

According to a preferred embodiment, the extraction means comprise an extraction guide, for example formed of an extraction rail 140, which extends in an input direction X.

For example, the input direction X comes out of the loading seat 58 when aligned with the exit 46b, and preferably, is a rectilinear direction.

The containers are suspended from the extraction rail 140 by means of the respective straws A and the extraction means are suitable for pushing the straws along the input direction X, in a direction of advancement IN.

To such purpose, for example, the extraction means comprise a pair of pushers provided with fingers 142 positioned on both sides of the extraction rail 140, spaced out along the input direction X, staggered along said input direction.

Preferably the pushers are driven by brushless motors.

The pushers are suitable for moving the fingers 142 in translation along the input direction X in the direction of advancement IN so as to engage and push the straws, for example corresponding to a group of containers.

In addition, the pushers are provided with a lifting and return movement, which is implemented when a pusher has completed its forward stroke, so as to pass over the row of hanging containers and go back, to extract further containers housed in the loading seat 58 of the loading unit 40 and make them advance.

In short, according to the embodiment illustrated said extraction means perform a "jumping" movement in which the fingers of the two pushers alternate in pushing each group of containers along the input direction X.

According to a preferred embodiment, the device 1 comprises a pre-sterilisation chamber 50, shielded from the leakage of X-rays, extending in an input direction X, positioned downstream of the loading unit 40 and upstream of the sterilisation group 20.

For example, the extraction means are housed in the pre-sterilisation chamber.

The sterilisation group 20 comprise an outer casing 22 which internally defines a sterilisation chamber, comprising a main chamber 24. In particular, a side wall 26 of the outer casing 22 presents the access for the containers coming from the input unit 40, moved by the extraction means.

The main chamber 24 extends mainly in a first sterilisation direction Y, preferably rectilinear.

Preferably the first sterilisation direction Y is inclined in relation to the input direction X, preferably orthogonal to it.

In addition, the pre-sterilisation chamber 50 helps to prevent the leakage of X-rays from the input unit 40.

The sterilisation group 20 further comprises at least one electron cannon suitable for emitting a cloud of electrons to sterilise the containers.

For an electron cannon, an emission cone of the electronic cloud and an emission axis which defines such emission cone is defined.

For example, the group 20 comprises two electron cannons 28a, 28b, having respective emission axes E1, E2.

Preferably the emission axes E1, E2 lie on the same horizontal plane or on planes parallel to the horizontal plane.

The cannons 28a, 28b are positioned in sequence in the first sterilisation direction Y, facing each other in the main chamber 24, positioned opposite one another.

The cannons 28a, 28b are positioned in sequence in the sense that the containers are struck first by the electronic cloud emitted by the first cannon and then by the electronic cloud emitted by the second cannon, or, in a transition zone only, they are simultaneously subject to the electronic cloud of the previous cannon and to the cloud of electrons of the next cannon.

The sterilisation group 20 further comprises support means of the containers along the main chamber 24 suitable for supporting said containers in the first sterilisation direction Y.

For example, said support means comprise a first rail 30 which extends in the first sterilisation direction Y, which the containers are hung from, for example by means of the straw A.

The sterilisation group 20 further comprises first means of advancing the containers suitable for moving the containers in the first sterilisation direction.

To change direction from the input direction X to the first sterilisation direction Y, the first extraction means act in conjunction with the means of advancement.

In particular, for example, the extraction means comprise a drum cam, positioned at the end of the pair of rails 140, suitable for pushing the containers into the main chamber 24, where they engage with the first means of advancement.

For example, said first means of advancement comprise a rotor element 32 which extends with its axis along the first sterilisation direction Y, rotatable so as to push the containers in said direction Y.

For example, the rotor element 32 surmounts the first rail 30 and engages the top of the straw A of the container C, projecting from the first rail 30, to push the container in the first sterilisation direction Y, Preferably, in addition, the sterilisation group 20 further comprises guide means suitable for guiding the body of the containers in the first sterilisation direction Y.

For example, said guide means comprise a pair of thread-like guides 34 extending in the first sterilisation direction Y, positioned below the first rail 30 and spaced out, so that the bodies B of the containers C are placed between them. Given the closeness of the guides 34, the oscillation of the containers is thereby limited or prevented.

The sterilisation chamber of the sterilisation group 20 further comprises a secondary chamber 36 which extends in a second sterilisation direction Z, incident to the first sterilisation direction Y, for example, preferably, orthogonal to it.

The rotor element 32 pushes the containers in the first sterilisation direction Y, as far as the end of the first rail 30, where the first means of advancement co-operate with the second means of advancement to change the direction of advancement from the first sterilisation direction Y to the second sterilisation direction Z.

The second means of advancement are suitable for moving the containers in the second sterilisation direction.

In addition, the sterilisation group 20 comprises 10 second support means suitable for supporting the containers in the second sterilisation direction Z.

For example, the second support means comprise a second rail 150 which extends from the zone where the first rail 30 ends, in the second sterilisation direction Z, and is suitable for hanging the containers C from, for example by means of the straw A.

In the transition zone between the first rail 30 and the second rail 150, the second means of advancement comprise a pusher 152 suitable for moving in alternated translatory movement in the second sterilisation direction Z.

The movement of the pusher 152 is synchronised with the movement of the rotor 32, for example by means of a rotating cam 154, connected by a belt or chain to the rotor element 32.

When the container C is left by the rotor element 32 at the end of the first rail 30, the second pusher 152 pushes said container along the second rail 102.

The containers hanging from the second rail 150 proceed in the second sterilisation direction Z as a result of the subsequent insertion of a further container in the tail, that is to say so that the subsequent container pushes the tail of the containers before it forward in the direction of advancement.

According to one embodiment variation (not shown), the second means of advancement are suitable for separately engaging sets of containers, to make them advance in the second sterilisation direction Z; For example, said second means of advancement are structurally and functionally similar to said first means of advancement.

The sterilisation group 20 further comprises a further electron cannon 28c, such as a third cannon 28c positioned along the second sterilisation direction Z, having an emission axis E3 incident to the horizontal plane, preferably orthogonal to it. In other words, the third cannon is positioned so that the emission axis E3 is parallel to the axis of the straw A of the container being treated.

It is therefore clear that the first sterilisation direction Y and the second sterilisation direction Z together define a sterilisation path along the sterilisation chamber.

The sterilisation device 1 further comprises an output unit 60, joined to the secondary chamber 36, downstream of the third cannon 28c in relation the direction of advancement of the containers being treated.

Preferably the output unit 60 is functionally and structurally similar to the input unit 40.

The treated containers pass from the sterilisation group 20 and in particular from its secondary chamber 36 to the output unit 60 and from this outside the device 1.

The sterilisation device comprises loading means suitable for loading a predefined number of containers C from the secondary chamber 36 to the loading seat of the input unit.

Preferably, said loading means comprise a pusher with a "jumping" movement similar to that described above.

According to a preferred embodiment, the device 1 comprises a post-sterilisation chamber 55, shielded from the leakage of X-rays, extending in the second sterilisation direction Z, positioned downstream of the sterilisation group and upstream of the output unit 60.

For example, the loading means are housed in the post-sterilisation chamber.

The post-sterilisation chamber also helps to prevent the leakage of X-rays from the output unit 60.

The containers C1 entering the input unit 40 are aligned one after another with the walls facing each other; the containers C1 are facing in columns that is.

The containers C1 are moved so that one or more containers C2 are housed in the loading seat 58 of the input unit 40. When the number of containers housed in the loading seat reaches a predefined number, the swivelling body 56 rotates to bring the loading seat 58 containing the containers C2 to align with the exit 46b and, preferably, the other loading seat 58, empty, to align with the entrance 46a for a further load.

The containers C3 contained in the loading seat 58 aligned with the exit 46b are moved so as to proceed along the input direction X, to then be deviated along the first sterilisation direction Y, In particular, the containers C4 cross the main chamber 20 aligned one behind the other in the first sterilisation direction Y, that is so to be facing in rows.

In the first sterilisation direction Y, the containers C4 undergo a first sterilisation by the first and second cannon 28a, 28b, the emission axes of which E1, E2 lie substantially on a horizontal plane.

In the first sterilisation direction Y, the containers C4 are positioned in rows, so that the walls B', B" of the body B are in front of the emission cone of the electron cannons 28a, 28b. In other words, the bodies B of the containers C4 are substantially coplanar and lie on a single plane in relation to which the emission axes E1, E2 are incident.

Such arrangement permits an excellent sterilisation of the walls B', B" of the body B of the containers C4 and, if necessary, of the gusset sides G where provided.

Downstream of the second cannon 28b, the containers being treated are deviated from the first sterilisation direction Y to the second sterilisation direction Z and at the same time moved along it so to enter and pass through the secondary chamber 36.

In particular, the containers C5 cross the secondary chamber 36 aligned one behind another with the walls facing each other; that is to say the containers C5 are facing in columns.

In the second sterilisation direction Z, the containers C5 undergo a second sterilisation by the third electron cannon 28c, the emission axis of which E3 is incident, in particular orthogonal to the horizontal plane.

In the second sterilisation direction Z, the containers C5 are positioned in columns, so that the axis of the straw A of the container is substantially parallel to the emission axis of the emission cone of the third cannon 28c.

Such arrangement permits an excellent sterilisation of the straw A of the container C.

The containers C5 are moved so that one or more containers C6 are housed in the loading seat of the output unit 60. When the number of containers housed in the loading seat reaches a predefined number, the swivelling body rotates to bring the loading seat containing the containers C6 to align with the exit and, preferably, the other loading seat, empty, to align with the entrance for a further load.

The containers C7 contained in the loading seat aligned with the exit are moved to the outside of the sterilisation device.

The change of direction in the advancement of the containers during sterilisation makes it possible to optimise the exposition times of the parts of these to the electron beams.

In particular, in the first sterilisation direction Y, the containers C4 are facing in rows and, given the arrangement of the electron cannons 28a, 28b, the sterilisation is particularly effective on the walls B', B" of the body B, which are particularly thin. The width dimension W of the containers C determines the transit time under the emission cones of the cannons 28a 28b of said containers.

In the second sterilisation direction Z, the containers C5 are facing in columns and, given the arrangement of the electron cannon 28c, the sterilisation is particularly effective inside the straw A. The thickness dimension T of the containers C determines the transit time under the emission cone of the cannon 28c of said containers.

Since the width W of the containers C is much greater than the thickness T of the same (the reason for which they are called thin walled containers), the exposition to the first sterilisation is much less than the exposition to the second sterilisation, with respect to the relative needs, since the walls of the container need a less prolonged sterilisation than the straw.

In general, along a sterilisation path, along which a first reference plane Pr1 and a further reference plane Pr3 are defined, separate from each other and incident to said sterilisation path, the first electron cannon 28a has an emission axis E1 lying on the first reference plane Pr1 and the further electron cannon 28c has an emission axis E3 lying on the further reference plane Pr3. The emission axis E3 of the further cannon 28c is inclined in relation to the sterilisation path, unlike the emission axis E1 of the first cannon 28a.

The container C can thereby be sterilised in different directions, to optimise the action of the electron clouds on different areas of the container.

Preferably In addition, a sterilisation system 100 comprises the sterilisation device, a support structure 102, which the device is placed on, for example raised off the ground, and an outer casing 104, which the device is contained in, suitable for acting as a screen to the leakage of radiation.

The outer casing 104 is composed of side walls in lead, which screen any radiation.

The casing 104 is fitted with a pair of seats 108, made in the side wall, at the point of the input unit and the output unit.

In the closed configuration, said units project outside the casing 104, to permit access of the containers to be sterilised or to allow the exit of the sterilised containers.

Preferably in addition, the structure 102 comprises a plurality of pillars 106, on which the casing 104 slides, to lower onto the device 1 and to contain it, or to lift up to permit servicing operations for example.

Innovatively, the low voltage electron beam sterilisation device according to the present invention is particularly suitable for treating thin-walled, flexible containers.

Advantageously, the device according to the invention is utilisable directly incorporated into the production plant since it greatly limits, in compliance with existing legislation, the leakage of radiation.

In particular, the design of the device according to the present invention follows the practical design rule known as the "3 bounce rule" according to which, any ray emitted by the cannons must bounce of the inner wall of the casing three times before getting out of the casing, thereby practically giving a zero value to the energy possessed.

in addition, Advantageously, it optimises the exposition times of the containers to the sterilisation, differentiating the exposure times according to the needs of the parts to be sterilised.

It is clear that a person skilled in the art may make modifications to the device described above.

For example, according to one embodiment variation, the electron cannon for the second sterilisation is on a plane with the cannon for the first sterilisation, while after the first sterilisation the containers are made to rotate in such a way as to position themselves with the straw parallel to the emission axis of the cannon for the second sterilisation.

According to a further embodiment variation, the input unit and/or output unit have more than two loading seats, for example angularly equidistant.

According to yet a further embodiment, the first sterilisation is performed by a single electron cannon.

According to yet a further embodiment, the second sterilisation is performed by two or more electron cannons.

Furthermore, according to one embodiment variation, the swivelling body of the input unit and/or output unit performs a rotation of 90° to bring the loaded containers into alignment for exit.

According to a further embodiment variation, the motor for driving the swivelling body is connected to it by a cinematic chain.

Such variations are also included within the sphere of protection as defined by the following claims.

What is claimed is:

1. A sterilisation device with electron beams for flexible thin wall containers comprising:
   an input or output unit shielded against radioactive emissions generated by the electron beams and comprising an outer casing and a swivelling body housed at least partially in a compartment inside the outer casing; and
   a sterilisation group having an inner sterilisation chamber, connected so as to be tight to radioactive emissions downstream of the input unit or upstream of the output unit, comprising at least one electron cannon suitable for emitting a beam of electrons in the sterilisation chamber;
   wherein the swivelling body is a solid cylindrical body swivelling upon command around a rotation axis and fitted with loading seats to bring a predefined number of containers from an outside environment into the sterilisation chamber, the loadings seats formed in the solid cylindrical body extend radially from the periphery of the solid cylindrical body towards the rotation axis of the solid cylindrical body, wherein remaining solid portions of cylindrical segments brush an inner surface of the compartment inside the outer casing, preventing leaks of radioactive emissions from the sterilisation chamber to the outside environment;
   wherein the sterilisation chamber comprises a main chamber extending along a first sterilisation axis, and a secondary chamber extending along a second sterilisation axis, incident to the first sterilisation axis; and wherein an emission axis of a second cannon is positioned on an emission plane defined by the emission axis of a first cannon and by a first sterilisation direction, on a side opposite the first cannon in relation to the first sterilisation direction.

2. The sterilisation device according to claim 1, wherein the swivelling body is fitted with at least two angularly distanced loading seats.

3. The sterilisation device according to claim 2, wherein the loading seats are positioned diametrically opposite to the rotation axis of the swivelling body.

4. The sterilisation device according to claim 1, comprising a pre-sterilisation chamber downstream of a loading unit and upstream of the sterilisation group, extending along an input axis, incident to the first sterilisation axis.

5. The sterilisation device according to claim 1, comprising a post-sterilisation chamber downstream of the sterilisation group, extending along an output axis coincident with the second sterilisation axis.

6. The sterilisation device according to claim 1, wherein a first cannon is positioned along the first sterilisation axis.

7. The sterilisation device according to claim 6, wherein a further cannon is positioned along the second sterilisation axis.

8. The sterilisation device according to claim 6, wherein a second cannon is positioned along the first sterilisation axis.

9. The sterilisation device according to claim 8, wherein an emission axis of a further cannon is inclined in relation to a second sterilisation direction, in a different way to the emission axis of the first cannon.

10. The sterilisation device according to claim 9, wherein the emission axis of the second cannon is positioned on an emission plane defined by the emission axis of the first cannon and by a first sterilisation direction, on a side opposite the first cannon in relation to the first sterilisation direction.

11. The sterilisation device according to claim 1, comprising:
a first support, positioned along a first sterilisation direction, suitable for guiding the containers so that they are positioned alongside each other in rows; and
a second support, positioned along a second sterilisation direction, suitable for guiding the containers so that they are positioned behind each other in columns.

12. The sterilisation device according to claim 1, comprising an input unit configured to introduce the containers to be sterilised to the sterilisation group and an output unit configured to remove the sterilised containers from the sterilisation group.

13. A method of sterilising flexible thin wall containers, comprising:
providing a sterilisation device with electron beams for flexible thin wall containers;
loading containers to be treated in a loading seat of a solid swivelling body of an input unit;
rotating the swivelling body to bring the containers into a sterilisation chamber;
extracting the containers from the loading seat facing the sterilisation chamber and making them advance along the sterilisation chamber;
emitting a cloud of electrons by means of an electron cannon into the sterilisation chamber; and
subjecting the containers to sterilisation by the cloud of electrons;
wherein the sterilisation device with electron beams for flexible thin wall containers comprises:
an input or output unit shielded against radioactive emissions generated by the electron beams and comprising an outer casing and a swivelling body housed at least partially in a compartment inside the outer casing; and
a sterilisation group having an inner sterilisation chamber, connected so as to be tight to radioactive emissions downstream of the input unit or upstream of the output unit, comprising at least one electron cannon suitable for emitting a beam of electrons in the sterilisation chamber;
wherein the swivelling body is a solid cylindrical body swivelling upon command around a rotation axis and fitted with loading seats to bring a predefined number of containers from an outside environment into the sterilisation chamber, the loadings seats formed in the solid cylindrical body extend radially from the periphery of the solid cylindrical body towards the rotation axis of the solid cylindrical body, wherein remaining solid portions of cylindrical segments brush an inner surface of the compartment inside the outer casing, preventing leaks of radioactive emissions from the sterilisation chamber to the outside environment;
wherein the sterilisation chamber comprises a main chamber extending along a first sterilisation axis, and a secondary chamber extending along a second sterilisation axis, incident to the first sterilisation axis; and
wherein an emission axis of a second cannon is positioned on an emission plane defined by the emission axis of a first cannon and by a first sterilisation direction, on a side opposite the first cannon in relation to the first sterilisation direction.

14. The method according to claim 13, comprising the steps of:
loading the sterilised containers in a loading seat of a swivelling body of an output unit, the loading seat facing towards the sterilisation chamber;
rotating the swivelling body to bring the containers from the sterilisation chamber to an external environment; and
extracting the containers from the loading seat facing the external environment.

15. A method of sterilising flexible thin wall containers, comprising the steps of:
providing a sterilisation device with electron beams for flexible thin wall containers;
inserting the containers in a sterilisation chamber and making them advance along the sterilisation chamber;
emitting a cloud of electrons by means of an electron cannon into the sterilisation chamber;
subjecting the containers to sterilisation by the cloud of electrons;
loading sterilised containers in a loading seat of a swivelling body of an output unit;
rotating the swivelling body to bring the containers to an external environment; and
extracting the containers from the loading seat facing the external environment and bringing them into the external environment;
wherein the sterilisation device with electron beams for flexible thin wall containers comprises:
an input or output unit shielded against radioactive emissions generated by the electron beams and comprising an outer casing and a swivelling body housed at least partially in a compartment inside the outer casing; and a sterilisation group having an inner sterilisation chamber, connected so as to be tight to radioactive emissions downstream of the input unit or upstream of the output unit, comprising at least one electron cannon suitable for emitting a beam of electrons in the sterilisation chamber;

wherein the swivelling body is a solid cylindrical body swivelling upon command around a rotation axis and fitted with loading seats to bring a predefined number of containers from an outside environment into the sterilisation chamber, the loadings seats formed in the solid cylindrical body extend radially from the periphery of the solid cylindrical body towards the rotation axis of the solid cylindrical body, wherein remaining solid portions of cylindrical segments brush an inner surface of the compartment inside the outer casing, preventing leaks of radioactive emissions from the sterilisation chamber to the outside environment;

wherein the sterilisation chamber comprises a main chamber extending along a first sterilisation axis, and a secondary chamber extending along a second sterilisation axis, incident to the first sterilisation axis; and wherein an emission axis of a second cannon is positioned on an emission plane defined by the emission axis of a first cannon and by a first sterilisation direction, on a side opposite the first cannon in relation to the first sterilisation direction.

16. The method according to claim 15, wherein the step of inserting the containers in a sterilisation chamber and making them advance along the sterilisation chamber comprises the step of:

loading the containers to be sterilised in a loading seat of a swivelling body of a loading unit, the loading seat facing the environment outside the sterilisation chamber;

rotating the swivelling body to bring the containers towards the sterilisation chamber; and extracting the containers from the loading seat facing the sterilisation chamber.

* * * * *